US008211489B2

(12) United States Patent
Pacetti

(10) Patent No.: US 8,211,489 B2

(45) **Date of Patent: *Jul. 3, 2012**

(54) METHODS FOR APPLYING AN APPLICATION MATERIAL TO AN IMPLANTABLE DEVICE

(75) Inventor: Stephen Pacetti, San Jose, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 657 days.

This patent is subject to a terminal disclaimer.

(21) Appl. No.: 12/331,301

(22) Filed: Dec. 9, 2008

(65) Prior Publication Data

US 2009/0181160 A1 Jul. 16, 2009

Related U.S. Application Data

(60) Provisional application No. 61/015,137, filed on Dec. 19, 2007.

(51) Int. Cl.

*B05D 1/02* (2006.01)
*B05D 3/04* (2006.01)
*A61L 33/00* (2006.01)

(52) U.S. Cl. ....... 427/2.25; 427/2.1; 427/2.24; 427/348; 427/377; 427/378; 427/421.1; 427/424; 427/427.1; 427/427.4; 427/427.5

(58) Field of Classification Search .................. 427/2.1, 427/2.12, 2.14, 2.16, 2.17, 2.21, 2.23, 2.24, 427/2.25, 2.3, 300, 348, 377, 378, 421.1, 427/422, 424, 425, 426, 427, 427.1, 427.2, 427/427.3, 427.4, 427.5, 427.6, 427.7, 438

See application file for complete search history.

(56) References Cited

U.S. PATENT DOCUMENTS

| | | | |
|---|---|---|---|
| 2,072,303 | A | 3/1937 | Herrmann et al. |
| 3,882,816 | A | 5/1975 | Rooz et al. |
| 3,995,075 | A | 11/1976 | Cernauskas et al. |
| 4,269,713 | A | 5/1981 | Yamashita et al. |
| 4,323,524 | A | 4/1982 | Snowden |
| 4,541,564 | A | 9/1985 | Berger et al. |
| 4,560,374 | A | 12/1985 | Hammerslag |
| 4,642,581 | A | 2/1987 | Erickson |
| 4,733,665 | A | 3/1988 | Palmaz |
| 4,800,882 | A | 1/1989 | Gianturco |
| 4,839,055 | A | 6/1989 | Ishizaki et al. |
| 4,865,879 | A | 9/1989 | Finlay |

(Continued)

FOREIGN PATENT DOCUMENTS

DE 1152920 8/1963

(Continued)

OTHER PUBLICATIONS

U.S. Appl. No. 61/051,126, filed Dec. 19, 2007, Pacetti.

(Continued)

*Primary Examiner* — Michael J Feely

(74) *Attorney, Agent, or Firm* — Workman Nydegger; Ron Devore

(57) ABSTRACT

Devices and methods for applying a coating to an implantable device are disclosed. A method for applying a coating to an implantable device is disclosed. The method includes positioning an implantable device relative to a material delivery apparatus. A spray pattern of an application material is produced using the material delivery apparatus. At least a portion of the spray pattern is deflected using a focusing assembly.

21 Claims, 6 Drawing Sheets

U.S. PATENT DOCUMENTS

| | | | | |
|---|---|---|---|---|
| 4,886,062 | A | 12/1989 | Wiktor | |
| 4,977,901 | A | 12/1990 | Ofstead | |
| 4,978,067 | A | 12/1990 | Berger et al. | |
| 5,112,457 | A | 5/1992 | Marchant | |
| 5,219,120 | A | 6/1993 | Ehrenberg et al. | |
| 5,328,471 | A | 7/1994 | Slepian | |
| 5,455,040 | A | 10/1995 | Marchant | |
| 5,464,650 | A | 11/1995 | Berg et al. | |
| 5,558,900 | A | 9/1996 | Fan et al. | |
| 5,578,073 | A | 11/1996 | Haimovich et al. | |
| 5,605,696 | A | 2/1997 | Eury et al. | |
| 5,628,730 | A | 5/1997 | Shapland et al. | |
| 5,667,767 | A | 9/1997 | Greff et al. | |
| 5,670,558 | A | 9/1997 | Onishi et al. | |
| 5,700,286 | A | 12/1997 | Tartaglia et al. | |
| 5,716,981 | A | 2/1998 | Hunter et al. | |
| 5,800,392 | A | 9/1998 | Racchini | |
| 5,824,049 | A | 10/1998 | Ragheb et al. | |
| 5,830,178 | A | 11/1998 | Jones et al. | |
| 5,837,313 | A | 11/1998 | Ding et al. | |
| 5,851,508 | A | 12/1998 | Greff et al. | |
| 5,858,746 | A | 1/1999 | Hubbell et al. | |
| 5,865,814 | A | 2/1999 | Tuch | |
| 5,873,904 | A | 2/1999 | Ragheb et al. | |
| 5,891,507 | A | 4/1999 | Jayaraman | |
| 5,971,954 | A | 10/1999 | Conway et al. | |
| 5,980,928 | A | 11/1999 | Terry | |
| 5,980,972 | A | 11/1999 | Ding | |
| 6,010,530 | A | 1/2000 | Goicoechea | |
| 6,015,541 | A | 1/2000 | Greff et al. | |
| 6,030,371 | A | 2/2000 | Pursley | |
| 6,042,875 | A | 3/2000 | Ding et al. | |
| 6,051,648 | A | 4/2000 | Rhee et al. | |
| 6,056,993 | A | 5/2000 | Leidner et al. | |
| 6,060,451 | A | 5/2000 | DiMaio et al. | |
| 6,080,488 | A | 6/2000 | Hostettler et al. | |
| 6,083,257 | A | 7/2000 | Taylor et al. | |
| 6,096,070 | A | 8/2000 | Ragheb et al. | |
| 6,099,562 | A | 8/2000 | Ding et al. | |
| 6,110,188 | A | 8/2000 | Narciso, Jr. | |
| 6,113,629 | A | 9/2000 | Ken | |
| 6,120,536 | A | 9/2000 | Ding et al. | |
| 6,120,904 | A | 9/2000 | Hostettler et al. | |
| 6,121,027 | A | 9/2000 | Clapper et al. | |
| 6,129,761 | A | 10/2000 | Hubbell | |
| 6,153,252 | A | 11/2000 | Hossainy et al. | |
| 6,156,373 | A | 12/2000 | Zhong et al. | |
| 6,165,212 | A | 12/2000 | Dereume et al. | |
| 6,306,176 | B1 | 10/2001 | Whitbourne | |
| 6,358,556 | B1 | 3/2002 | Ding et al. | |
| 6,358,567 | B2 | 3/2002 | Pham et al. | |
| 6,364,903 | B2 | 4/2002 | Tseng et al. | |
| 6,368,658 | B1 | 4/2002 | Schwarz et al. | |
| 6,395,326 | B1 | 5/2002 | Castro et al. | |
| 6,407,009 | B1 | 6/2002 | You et al. | |
| 6,426,145 | B1 | 7/2002 | Moroni | |
| 6,503,954 | B1 | 1/2003 | Bhat et al. | |
| 6,534,112 | B1 | 3/2003 | Bouchier et al. | |
| 6,555,157 | B1 | 4/2003 | Hossainy et al. | |
| 6,696,121 | B2 | 2/2004 | Jung, Jr. et al. | |
| 6,818,247 | B1 | 11/2004 | Chen et al. | |
| 6,861,088 | B2 | 3/2005 | Weber et al. | |
| 7,504,125 | B1 * | 3/2009 | Pacetti et al. | 427/2.24 |
| 7,951,428 | B2 * | 5/2011 | Hoerr et al. | 427/483 |
| 8,007,858 | B2 | 8/2011 | Pacetti et al. | |
| 2004/0062875 | A1 | 4/2004 | Chappa et al. | |
| 2006/0198940 | A1 | 9/2006 | McMorrow | |
| 2007/0128343 | A1 | 6/2007 | Chappa | |
| 2007/0254091 | A1 | 11/2007 | Fredrickson et al. | |
| 2009/0136556 | A1 * | 5/2009 | Pacetti et al. | 424/422 |
| 2009/0181159 | A1 | 7/2009 | Pacetti | |

FOREIGN PATENT DOCUMENTS

| | | |
|---|---|---|
| EP | 0665023 | 8/1995 |
| EP | 0970711 | 1/2000 |
| GB | 1455862 | 11/1976 |
| WO | WO 91/12846 | 9/1991 |
| WO | WO 97/45105 | 12/1997 |
| WO | WO 99/63981 | 12/1999 |
| WO | WO 00/02599 | 1/2000 |
| WO | WO 00/12147 | 3/2000 |
| WO | WO 00/64506 | 11/2000 |
| WO | WO 01/01890 | 1/2001 |
| WO | WO 01/45763 | 6/2001 |
| WO | WO 2005/065843 | 7/2005 |
| WO | WO 2007/089881 | 8/2007 |
| WO | WO 2009/085618 | 7/2009 |
| WO | WO 2009/085619 | 7/2009 |

OTHER PUBLICATIONS

U.S. Appl. No. 61/051,137, filed Dec. 19, 2007, Pacetti.

SONO-TEK Accu Mist—For Single Stent Coating Applications, Internet Citation, Retrieved from the Internet on Apr. 1, 2005.

SONO-TEK Accu Mist—For Single Stent Coating Applications, Internet Citation, Retrieved from the Internet on Feb. 9, 2007.

SONO-TEK Micro Mist—For Stent Coating, Internet Citation, Retrieved from the Internet on Feb. 9, 2007.

SONO-TEK Accu Mist for Stent Coating [online] XP002529453 Retrieved from Internet: URL:http;//www.sono-tek.com/print.php-?page=41> [retrieved on May 25, 2009] Product description of AccuMist ultrasonic spray nozzle for stent coating. The whole document.

Peter J. Tarcha et al. "The Application of Ink-Jet Technology for the Coating and Loading of Drug-Eluting Stents"Annals of Biomedical Engineering, Kluwer Academic Publishers-Plenum Publishers, NE, vol. 35, No. 10, Jul. 19, 2007 pp. 1791-1799, XP019522973.

U.S. Appl. No. 12/331,290, Jun. 21, 2011, Office Action.

U.S. Appl. No. 09/894,293, filed Jun. 27, 2001, Roorda et al.

Barath et al., *Low Dose of Antitumor Agents Prevents Smooth Muscle Cell Proliferation After Endothelial Injury*; JACC vol. 13, No. 2; Feb. 1989:252A (Abstract).

Dichek et al., *Seeding of Intravascular Stents With Genetically Engineered Endothelial Cells*, Circulation 1989; 1347-1353.

Forester et al., *A Paradigm for Restenosis Based on Cell Biology: Clues for the Development of New Preventive Therapies*; J. Am. Coll. Cardio. 1991; 17:758-769.

Matsumaru et al.; *Embolic Materials for Endovascular Treatment of Cerebral Lesions*; J. Biomatter Sci. Polymer Edn., vol. 8, No. 7 (1997) pp. 555-569.

Miyasaki et al., *Antitumor Effect of Implanted Ethylene-Vinyl Alcohol Copolymer Matrices Containing Anticancer Agents on Ehrlich Ascites Carcinoma and P388 Leukemia in Mice*; Chem. Pharm. Bull. 33(6) (1985) pp. 2490-2498.

Miyazawa et al., *Effects of Pemirolast and Tranilast on Intimal Thickening After Arterial Injury in the Rat*, J. Cardiovasc. Pharmacol. (1997) pp. 157-162.

Ohsawa et al., *Preventive Effects of an Antiallergic Drug, Pemirolast Potassium, on Restenosis After Percutaneous Transluminal Coronary Angioplasty*; American Heart Journal (1998) pp. 1081-1087.

Shigeno, *Prevention of Cerebrovascular Spasm by Bosentan, Novel Endothelin Receptor*; Chemical Abstract 125:212307 (1996).

U.S. Appl. No. 10/040,538, Mar. 4, 2004, Office Action.

U.S. Appl. No. 10/040,538, Sep. 30, 2004, Office Action.

U.S. Appl. No. 10/040,538, Jul. 5, 2005, Office Action.

U.S. Appl. No. 10/040,538, Apr. 19, 2006, Office Action.

U.S. Appl. No. 10/040,538, Jan. 5, 2007, Office Action.

U.S. Appl. No. 10/040,538, Jan. 2, 2009, Notice of Allowance.

U.S. Appl. No. 12/331,290, Nov. 16, 2011, Office Action.

U.S. Appl. No. 363,538, Aug. 21, 2009, Office Action.

U.S. Appl. No. 12/363,538, Dec. 3, 2009, Office Action.

U.S. Appl. No. 12/363,538, Jun. 7, 2010, Office Action.

U.S. Appl. No. 12/363,538, May 16, 2011, Notice of Allowance.

U.S. Appl. No. 12/363,538, Aug. 10, 2011, Issue Notification.

* cited by examiner

METHODS FOR APPLYING AN APPLICATION MATERIAL TO AN IMPLANTABLE DEVICE

CROSS-REFERENCE TO RELATED APPLICATIONS

This application claims the benefit of and priority to U.S. Provisional Patent Application No. 61/015,137, filed Dec. 19, 2007, and entitled "Methods For Applying An Application Material To An Implantable Device" which is incorporated herein by reference in its entirety. This application also incorporates U.S. Provisional Patent Application No. 61/015,126, filed Dec. 19, 2007, and entitled "Methods For Applying An Application Material To An Implantable Device", by reference in its entirety.

FIELD OF THE INVENTION

The present invention relates generally to medical devices, and more particular to methods for applying an application material to an implantable device.

BACKGROUND OF THE INVENTION

Percutaneous transluminal coronary angioplasty (PTCA) is a procedure for treating heart disease. This procedure generally entails introducing a balloon catheter assembly into the cardiovascular system of a patient via the brachial or femoral artery and advancing the balloon catheter assembly through the coronary vasculature until the balloon is positioned across an occlusive lesion. Once in position across the lesion, the balloon is inflated to a predetermined size to radially compress against the atherosclerotic plaque of the lesion to remodel the vessel wall. Subsequently, the balloon is deflated to allow the balloon catheter assembly to be withdrawn from the vasculature.

While PTCA is widely used, it suffers generally from two unique problems. First, the blood vessel may suffer acute occlusion immediately after or within the initial hours after the dilation procedure. Such occlusion is referred to as "abrupt closure." Abrupt closure occurs in approximately five percent of cases in which PTCA is employed. The primary mechanisms of abrupt closures are believed to be elastic recoil, arterial dissection, vasospasm, and/or thrombosis. The second problem associated with this procedure is the re-narrowing of an artery after an initially successful angioplasty. This re-narrowing is referred to as "restenosis," which typically occurs within the first six months after angioplasty. Restenosis is believed to be due to, among other things, the proliferation and migration of cellular components from the arterial wall, as well as through geometric changes in the arterial wall referred to as "remodeling."

To reduce occlusion of the artery, and the development of thrombosis and/or restenosis, an expandable interventional device or prosthesis, one example of which includes a stent, may be implanted in the lumen to maintain the vascular patency. Additionally, to better effectuate the treatment of such vascular disease, it may be preferable to load an intraluminal device or prosthesis with one or more beneficial agents, such as antiproliferatives, for delivery to a lumen. One commonly-applied technique for the local delivery of a drug is through the use of a polymeric carrier coated onto the surface of a stent. Such conventional methods and products generally have been considered satisfactory for their intended purpose.

However, implantable devices, such as stents, may be difficult to coat without webbing, cobwebs, or other defects due to their generally intricate geometry. They may also be difficult to uniformly coat (i.e. on the ablumenal, luminal, and sidewall surfaces). Because of these challenges, many commercialized drug eluting stents are being coated by a spray process. However, spray coating may suffer generally from the following: reduced coating speed, reproducibility, and/or coating efficiency (i.e. the amount of material sprayed actually coating the device).

Accordingly, it may be desirable to provide methods for applying an application material to an implantable device.

BRIEF SUMMARY

An embodiment of a method of coating an implantable device is described. The method includes positioning an implantable device relative to a material delivery apparatus. A spray pattern of an application material is produced using the material delivery apparatus. At least a portion of the spray pattern is deflected using a focusing assembly comprising at least one focusing jet.

Another embodiment of a method of coating an implantable device is disclosed. The method includes positioning an implantable device relative to a material delivery apparatus. A spray pattern of an application material is produced using the material delivery apparatus. At least a portion of the spray pattern is deflected using a focusing assembly comprising an annular focusing jet.

In some embodiments, the at least one focusing jet deflects at least a portion of the spray pattern toward a central axis. The at least one focusing jet, in further embodiments, deflects at least a portion of the spray pattern toward the implantable device.

Positioning an implantable device relative to a material delivery apparatus in some embodiments includes positioning the implantable device a predetermined distance relative to the material delivery apparatus. In further embodiments, the predetermined distance is selected to facilitate at least partial drying of the application material prior to contact with the implantable device. The implantable device, in still further embodiments, is moved relative to a material delivery apparatus during spraying by a combination of translation and/or rotational motion.

In some embodiments, the at least one focusing jet is positioned relative to the material delivery apparatus and the implantable device. The at least one focusing jet, in further embodiments, deflects at least a portion of the spray pattern using at least one deflecting fluid selected from the group consisting of air, dry air, nitrogen, argon, helium, neon, carbon dioxide, oxygen, sulfur hexafluoride, water vapor, and/or gas at a controlled humidity. In still further embodiments, the deflecting fluid used to direct the application material is above ambient temperature to facilitate drying.

The material delivery apparatus, in some embodiments, includes a material delivery device and an ultrasonic generator configured to atomize at least a portion of the application material. In further embodiments, the application material includes a radiopaque material. The application material, in still further embodiments, includes a contrast agent for magnetic resonance imaging. In yet further embodiments, the application material includes a solvent. The application material, in some embodiments, includes a polymeric material. In further embodiments, the application material includes at least one bioactive agent that is an anti-proliferative, anti-inflammatory, antineoplastic, antiplatelet, anti-coagulant, anti-fibrin, antithrombonic, antimitotic, antibiotic, antiallergic or antioxidant drug.

In some embodiments, the application material is atomized by ultrasonic energy, by application of a high-pressure stream of gas, by centrifugal action, by electric potential, and/or by other atomization processes. The implantable device, in further embodiments, is a closure element. In still further embodiments, the implantable device is a stent.

An annular focusing jet, in some embodiments, receives a deflecting fluid through an input port and directs the fluid from a chamber through at least one opening along an inner surface of the focusing jet. In further embodiments, the at least one opening has a dimension that is smaller than a dimension of the chamber and/or a dimension of the input port. The at least one opening of the annular focusing jet, in still further embodiments, is circumferentially uniform.

It is to be understood that both the foregoing general description and the following detailed description are exemplary and are intended to provide further explanation of the invention claimed.

The accompanying Figures, which are incorporated in and constitute part of this specification, are included to illustrate and provide a further understanding of the method and system of the invention. Together with the description, the Figures serve to explain the principles of the invention.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings.

Figure 1:
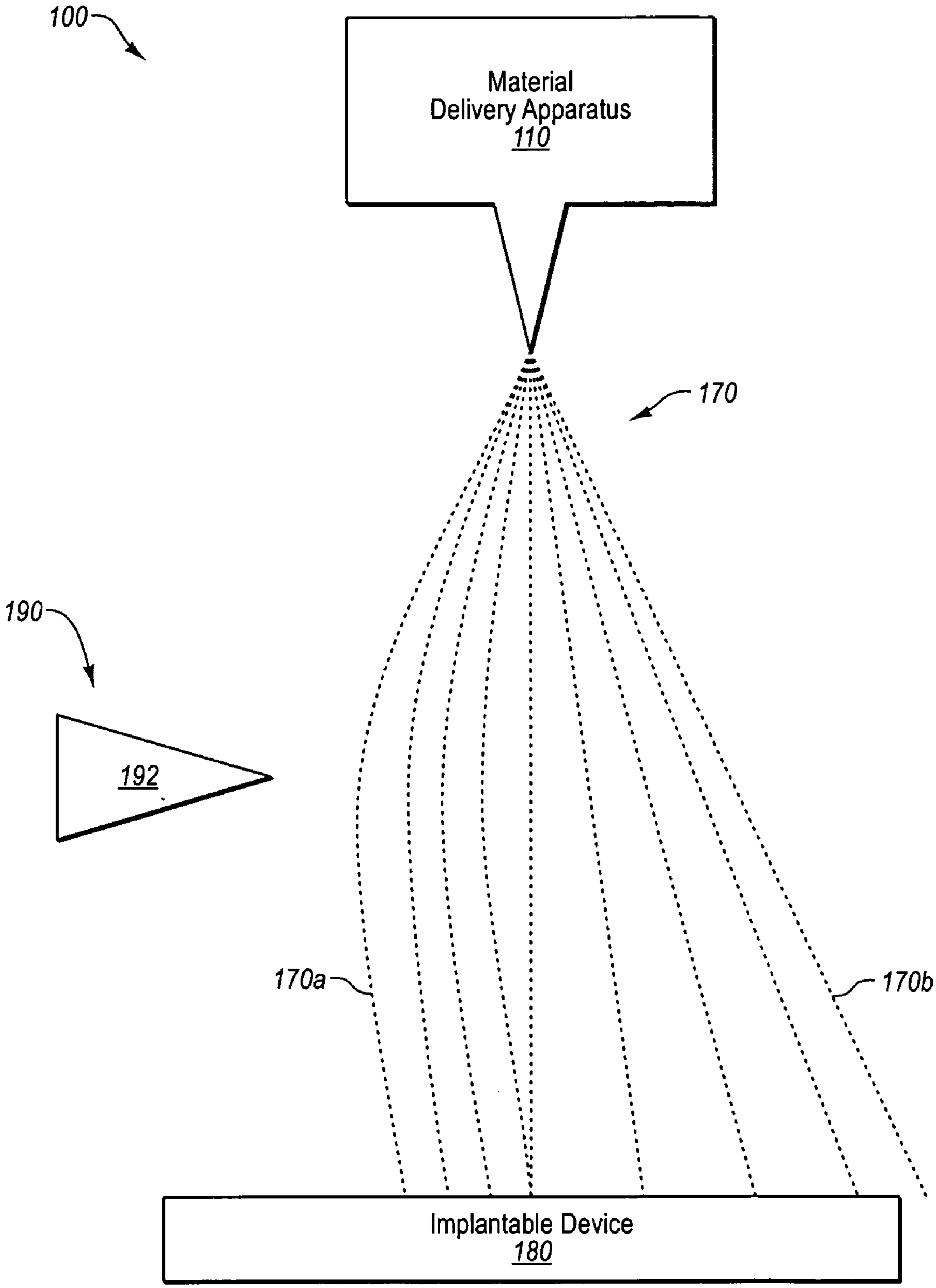
FIG. 1 illustrates a block diagram of an embodiment of a system for applying an application material to an implantable device, in accordance with the present invention.

It should be noted that the figures are not drawn to scale and that elements of similar structures or functions are generally represented by like reference numerals for illustrative purposes throughout the figures. It also should be noted that the figures are only intended to facilitate the description of embodiments of the present invention.

DETAILED DESCRIPTION

Methods and apparatus for coating an implantable device are disclosed. In one embodiment, a focusing assembly may be used in conjunction with any material delivery apparatus for coating implantable devices, for example drug eluting stents, closure elements, and/or other implantable devices. Embodiments of a focusing assembly may be used in conjunction with a material delivery apparatus in order to generally focus the spray pattern of an application material. Both the coating efficiency and the spray coating rate may be improved through use of the system and methods of described herein.

In one embodiment, a fluid path of a coating material may be produced. The fluid path may be deflected by a focusing assembly. In some embodiments, the focusing assembly may include at least one focusing jet. In other embodiments, the focusing assembly may include an annular focusing jet. In further embodiments, at least one of the focusing assembly, the material delivery apparatus, the implantable device, and/or other components of the system has a positive or negative electric charge to further deflect the fluid path. In still further embodiments, the coating solution may be atomized by ultrasonic energy, by application of a high-pressure stream of gas, by centrifugal action, by electric potential, and/or by other atomization procedures.

Deflecting a fluid path and/or atomizing a coating solution by electric potential may be accomplished as disclosed in U.S. Patent Application No. 61/015,126, filed Dec. 19, 2007, and entitled "METHODS FOR APPLYING AN APPLICATION MATERIAL TO AN IMPLANTABLE DEVICE", which is incorporated herein by reference in its entirety. For example, at least a portion of the focusing assembly may have a positive or a negative charge sufficient to facilitate atomization of the coating solution. In another instance, the focusing assembly may have a positive or a negative charge while the implantable device has an opposing charge to facilitate the deflection of the fluid path toward and/or away from the implantable device.

These results, whether individually or collectively, can be achieved, according to one embodiment of the present invention, by employing methods, systems, and/or apparatus as shown in the figures and described in detail below.

Turning now to the drawings, FIG. 1 illustrates a block diagram of an embodiment of a system 100 for applying an application material 170 to an implantable device 180, in accordance with the present invention. The system 100 includes a material delivery apparatus 110 that may apply an application material 170 to an implantable device 180 and a focusing apparatus 190 that may deflect or change a spray pattern of the application material 170. Material delivery apparatus 110 may generally include an ultrasonic material delivery apparatus, an external air assisted material delivery apparatus, an electrospray material delivery apparatus, other material delivery apparatuses, and/or combinations thereof. The present embodiment illustrates a single material delivery apparatus 110, although a plurality of material delivery apparatuses 110 may be used.

In the present configuration, focusing apparatus 190 includes one focusing jet 192. The focusing jet 192 may deflect or change the spray pattern of the application material 170. For example, the focusing assembly 190 may deflect a first portion of the application material 170*a*. While a second portion of the application material 170*b*, may remain undeflected by the focusing assembly 190.

Deflecting the spray pattern of the application material 170 may reduce the amount of application material 170 that may be wasted when applying the application material 170 without a focusing assembly 190. For example, the second portion of the application material 170*b* may not entirely contact the implantable device 180.

The spray pattern of the application material 170 may be deflected or changed using a deflecting fluid. The deflecting fluid may include air, dry air, nitrogen, argon, helium, neon, carbon dioxide, oxygen, sulfur hexafluoride, water vapor, and/or gas at a controlled humidity. The deflecting fluid used to direct the application material may optionally be heated above ambient temperature to facilitate at least partial drying of the application material 170.

The application material 170 may include beneficial agents, imaging materials, polymers, solvents, and/or other application materials. For example, the material delivery apparatus 110 can load the beneficial agent directly onto the implantable device 180 or alternatively, the beneficial agent can be loaded onto a base material layer that is first applied to a surface of the implantable device 180. For example, and without limitation, a base coating, such as a binder or suitable polymer, can be applied to a selected surface of the implantable device 180 such that a desired pattern is formed on the implantable device 180 surface. A beneficial agent is then applied directly to the pattern of the base material.

Alternatively, a suitable base coating capable of retaining beneficial agent therein can be applied uniformly over the surface of the implantable device 180 using the system 100, and then selected portions of the base coating can be loaded with the beneficial agent. A greater amount of beneficial agent could be loaded over a unit surface area of the base coating intended to have a greater local a real density and a lower amount of beneficial agent could be loaded over a unit surface area intended to have a lower local a real density.

In yet another embodiment of the present invention, the beneficial agent can be applied directly to the surface of the implantable device 180. Generally, a binder or similar component can be used to ensure sufficient adhesion. For example, this coating technique can include admixing the beneficial agent with a suitable binder or polymer to form a coating mixture, which is then coated onto the surface of the implantable device 180. The coating mixture is prepared in higher or lower concentrations of beneficial agent as desired, and then applied to selected portions of the implantable device 180 appropriately.

The beneficial agents, such as any compound, mixture of compounds, or composition of matter consisting of a compound, which produces a beneficial or useful result, may be expensive. Reducing overspray and increasing the coating efficiency can reduce the cost of coating implantable devices.

The beneficial agents or application material 170 can be a polymer, a marker, such as a radiopaque dye or particles, an MRI contrast agent, or can be a drug, including pharmaceutical and therapeutic agents, or an agent including inorganic or organic drugs without limitation. The agent or drug can be in various forms such as uncharged molecules, components of molecular complexes, nano or microparticles, pharmacologically-acceptable salts such as hydrochloride, hydrobromide, sulfate, laurate, palmitate, phosphate, nitrate, borate, acetate, maleate, tartrate, oleate, and salicylate.

In addition to the general description of beneficial agents provided above, the beneficial agents may generally include analgesics, antipyretics, antiasthamatics, antibiotics, antidepressants, antidiabetics, antifungal agents, antihypertensive agents, anti-inflammatories including non-steroidal and steroidal, antineoplastics, antianxiety agents, immunosuppressive agents, antimigraine agents, sedatives, hypnotics, antianginal agents, antipsychotic agents, antimanic agents, antiarrhythmics, antiarthritic agents, antigout agents, anticoagulants, thrombolytic agents, antifibrinolytic agents, hemorheologic agents, antiplatelet agents, anticonvulsants, antiparkinson agents, antihistamines, anti-restenosis agents, antipruritics, agents useful for calcium regulation, antibacterial agents, antiviral agents, antimicrobials, anti-infectives, bronchodilators, steroidal compounds and hormones, or combinations thereof. Preferably, the active agent comprises at least one of rapamycin, rapamycin analog, zotarolimus, ABT-578, sirolimus, everolimus, biolimus, temsirolimus, novolimus, myolimus, AP23573, deforolimus, dexamethasone, prednisone, hydrocortisone, estradiol, acetaminophen, ibuprofen, naproxen, sulidac, heparin, taxol, paclitaxel, and/or combinations thereof. Additional drugs can be found in co-pending U.S. patent application Ser. No. 10/703,891, filed Nov. 07, 2003, entitled "Prosthesis with Multiple Drugs Applied Separately by Fluid Jet Application in Discrete Unmixed Droplets", the disclosure of which is incorporated herein by this reference.

Imaging materials may include materials, such as radiopaque materials. Examples of radiopaque materials may include high-density materials such as gold, platinum, platinum/iridium, tungsten, hafnium, rhenium, zirconium, niobium, barium salts, bismuth compounds, and/or other radiopaque materials. As used herein, the term radiopaque may include partial radiopacity as well as total radiopacity. Examples of MRI contrast agents include chelates of gadolinium, superparamagnetic iron compounds, ion oxides, transition metal oxides, transition metal ions, and paramagnetic ions.

Other application materials may include polymeric materials comprised of phosphorylcholines, phosphorylcholine linked macromolecules, phosphoryl choline derivatized acrylates and methacrylates, polyolefins, poly(methacrylates), polyurethanes, polyesters, polyanhydrides, polyphosphazenes, polyacrylates, acrylic polymers, poly(lactide-coglycolides) (PLGA), poly(L-lactide), polylactic acids (PLA), poly(hydroxybutyrates), poly(hydroxybutyrate-co-valerates), polydioxanones (PDO), polyorthoesters, polyglycolide, polyglycolic acid (PGA), polycaprolactone (PCL), poly(glycolide-co-trimethylene carbonates), polyphosphoesters, polyphosphoester urethanes, poly(amino acids), cyanoacrylates, poly(trimethylene carbonate), polyorthoesters, poly(iminocarbonate), tyrosine derived polycarbonates, tyrosine derived polyarylates, polyalkylene oxalates, poly(iminocarbonates), aliphatic polycarbonates, fibrins, fibrinogens, cellulosics, starchs, collagens, polycarbonate urethanes, polyisoprenes, polyisobutylenes, polybutadienes, poly(styrene-b-isobutylene-b-styrene), polyethylenes, plasticized poly(ethylene terephthalates), poly(ethylene terepthalates), poly(methylmethacrylates), ethylene ethylacrylates, poly(ethyl hexylacrylates), plasticized ethylene vinylacetates, poly(vinyl acetates), ethylene vinyl acetates, ethylene vinyl alcohols, poly(vinyl alcohols), poly(butyral), cross-linked poly(vinyl alcohols), cross-linked poly(vinyl butyrates), poly(vinylbutyrates), poly(butylmethacrylates), poly(vinyl chlorides), ethylene vinylchloride copolymers, poly(vinyl fluoride), poly(vinylidene fluoride), poly(vinylidene fluoride-co-hexafluoropropylene), poly(vinylidene fluoride-co-chlorotrifluoroethylene), silicones, polysiloxanes, substituted polysiloxanes, poly(ethylene oxides), poly (ethylene glycols) (PEG), poly(butylene terepthalate-co-PEG), PCL-co-PEG, PLA-co-PEG, poly(vinyl acetals), poly (vinyl acetates), polyamides, poly(vinyl pyrrolidones), poly (acrylamides), poly(vinyl esters), copolymers thereof, polymer derivatives thereof, and/or combinations thereof.

Implantable devices 180 may include various interventional devices that can refer broadly to any device suitable for intraluminal delivery or implantation. For purposes of illustration and not limitation, examples of such interventional devices include stents, grafts, stent-grafts, filters, and the like. As is known in the art, such devices may comprise one or more prostheses, each having a first cross-sectional dimension or profile for the purpose of delivery and a second cross-sectional dimension or profile after deployment. Each prosthesis may be deployed by known mechanical techniques such as balloon expansion deployment techniques, or by electrical or thermal actuation, or self-expansion deployment techniques, as well known in the art. Examples of such for purpose of illustration include U.S. Pat. No. 4,733,665 to Palmaz; U.S. Pat. No. 6,106,548 to Roubin et al.; U.S. Pat. No. 4,580,568 to Gianturco; U.S. Pat. No. 5,755,771 to Penn et al.; and U.S. Pat. No. 6,033,434 to Borghi, all of which are incorporated herein by reference.

Figure 2:
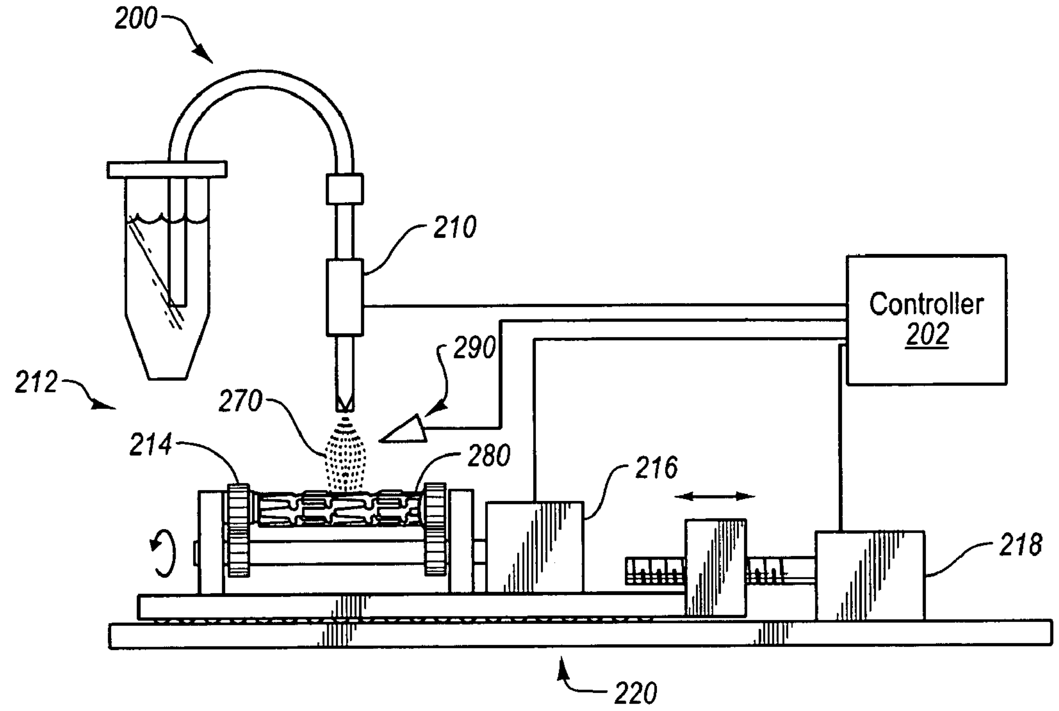
FIG. 2 illustrates a schematic representation of an embodiment of a system for applying an application material to an implantable device, in accordance with the present invention.

More specifically, the implantable device can be an expanded or unexpanded prosthesis, such as the stent illustrated in FIG. 2. The underlying structure of the prosthesis can be virtually any structural design and the prosthesis can be composed of any suitable material such as, but not limited to, stainless steel, "MP35N," "MP20N," cobalt chromium alloy, Haynes 25, cobalt chrome L-605, Haynes 88, elastinite (Nitinol), tantalum, nickel-titanium alloy, tantalum tungsten alloy, tantalum tungsten niobium alloy, niobium alloy, rhenium alloy, platinum-iridium alloy, gold, magnesium, polymer, ceramic, tissue, or combinations thereof. "MP35N" and "MP20N" are understood to be trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium and 10% molybdenum. The prosthesis can be made from bioabsorbable or biostable polymers. In some embodiments, the surface of the prosthesis can include one or more reservoirs or cavities formed therein, as described further below.

The prosthesis can be fabricated utilizing any number of methods known in the art. For example, the prosthesis can be fabricated from a hollow or formed tube that is machined using lasers, electric discharge milling, chemical etching or other known techniques. Alternatively, the prosthesis can be fabricated from a sheet that is rolled into a tubular member, or formed of a wire or filament construction as known in the art.

Furthermore, the implantable devices can be drug eluting stents, drug delivery catheters, grafts, stent-grafts, arterial wraps, drug delivery balloons, guidewires, orthopedic implants, dental implants, fixation screws, indwelling catheters, ocular implants, pharmacotherapeutic implants, heart valves, blood-contacting components of extracorporeal devices, staples, sutures, filters, needles, tubes, coils, wires, clips, screws, sensors, plates, shunts, conduits, portions thereof, PFO closure devices, vascular closure devices, closure elements for engaging tissue, combinations thereof, and/or other implantable devices.

In one embodiment, the implantable device 180 may include an endoprosthesis for controlling the release of an active agent therefrom. Such an endoprosthesis can include the following: a supporting metal structure configured and dimensioned to be used within a body of a human; a porous body disposed on and at least partially covering the supporting metal structure, the porous body including a first biocompatible material having a plurality of pores; a therapeutically effective amount of an active agent disposed within the pores, the therapeutically effective amount of the active agent being capable of treating and/or preventing a disease; an elution rate controlling matrix disposed within the porous body so as to contain the active agent within the pores, the matrix material including a polymeric biocompatible material that at least partially controls an elution rate of the active agent from the pores; and the pores each having a dimension that is configured to at least partially determine the elution rate.

In one embodiment, the implantable device may include a stent for controlling the release of an active agent therefrom. Such a stent can include the following: a superelastic metal structure configured and dimensioned as a stent to be used within a lumen of an animal; a porous body disposed on and at least partially covering the superelastic metal structure, the porous body including a first biocompatible material having a plurality of pores; a therapeutically effective amount of an active agent disposed within at least a portion of the pores, the therapeutically effective amount of the active agent being capable of treating and/or preventing a disease; and an elution rate controlling matrix disposed on at least one surface of the porous body so as to contain the active agent within the at least a portion of the pores, the matrix material including a second biocompatible material that controls an elution rate of the active agent from the pores. Optionally, the porous body is integrated with the supporting structure.

In another embodiment, the implantable device 180 includes an endoprosthesis for controlling the release of an active agent therefrom. Such an endoprosthesis can include the following: a supporting metal structure configured and dimensioned to be used within a body of a human; a porous body disposed on and at least partially covering the supporting metal structure, the porous body including a first biocompatible material having a plurality of pores; a therapeutically effective amount of an active agent disposed within the pores, the therapeutically effective amount of the active agent being capable of treating and/or preventing a disease; an elution rate controlling matrix disposed on top of the porous body so as to contain the active agent within the pores, and the matrix material including a polymeric biocompatible material that at least partially controls an elution rate of the active agent from the pores.

In yet another embodiment, the implantable device 180 may include an endoprosthesis for controlling the release of an active agent therefrom. Such an endoprosthesis can include the following: a supporting metal structure configured and dimensioned to be used within a body of a human; a polymeric basecoat disposed on at least a portion of or at least partially covering the supporting metal structure; a blend of an active agent combined with a polymeric material disposed on at least a portion of the basecoat to form a drug reservoir layer, with a therapeutically effective amount of an active agent combined into the reservoir layer, the therapeutically effective amount of the active agent being capable of treating and/or preventing a disease; and an optional elution rate controlling matrix disposed on top of the drug reservoir layer to at least partially control an elution rate of the active agent.

FIG. 2 illustrates a schematic representation of an embodiment of a system 200 for applying an application material 270 to an implantable device 280, in accordance with the present invention. The system 200 of this embodiment may be functionally similar to that of the system 100 previously described above and shown in FIG. 1 in most respects, wherein certain features will not be described in relation to this embodiment wherein those components may function in the manner as described above and are hereby incorporated into this alternative embodiment described below. Like structures or components are given like reference numerals.

The system 200 may include a material delivery apparatus 210 that may apply an application material 270 to an implantable device 280. The delivery or loading of the application material 270 to the implantable device 280 can be varied through use of a controller 202, a positioning assembly 212, and/or the focusing assembly 290 that may deflect or change a spray pattern of the application material 270. For instance, the controller 202 can be programmed with the structural configuration of the implantable device 280 and control delivery or loading the application material 270 through controlling the operation of the material delivery apparatus 210, the positioning assembly 212 and/or the focusing assembly 290. In this manner, the invention reduces or eliminates webbing and bridging of application material across openings or gaps within the structure of the prosthesis and minimizes waste.

The positioning assembly 212 can include a driver assembly 220 that creates relative movement between a holder 214 configured to support the implantable device 280 and the material delivery apparatus 210. As mentioned above, the controller 202 in communication with the driver assembly 220 can define a dispensing path of relative movement between the material delivery apparatus 210 and the holder 214. The controller 202 can also communicate with the material delivery apparatus 210 for selectively dispensing application material 270 in a selected format along the dispensing path onto a selected portion of the implantable device 280 supported by the holder 214. In one configuration, the holder 214 supporting the implantable device 280 is moveable while the material delivery apparatus 210 remains stationary during dispensing of application material 270. However, in another aspect of the invention the holder 214 supporting the implantable device 280 remains stationary while the material delivery apparatus 210 moves along the dispensing path. Alternatively, both the holder 214 and material delivery apparatus 210 are moveable.

In another configuration, the system can include a detector or sensor to detect when the material delivery apparatus 210 is aligned with the selected portions of the implantable device 280. Such a detector or sensor can be an optical detector, e.g., linear array detector or infrared detector, ultrasound probe, temperature probe, camera, capacitance meter, electrometer, hall-effect probe, and the like, or any other sensor or detector known in the art for detection.

With continued reference to FIG. 2, the positioning assembly 212 can further include a rotating driver 216 and a longitudinal driver 218. The holder 214 may be rotated through the rotation driver 216, which can include a motor. For instance, the rotating driver 216 can be activated to produce a constant angular velocity on the implantable device 280 during application material delivery. Similarly, the longitudinal driver 218 can control advancement of the implantable device 280 longitudinally past the material delivery apparatus 210. Again, the longitudinal driver 218 can include a motor.

Through the system 200, application material 270 can be loaded or delivered to an implantable device 280 in a controlled manner. The system 200 enables and facilitates relative movement between the material application apparatus 210 and the implantable device 280 to define a dispensing path along which the application material can be selectively dispensed. The focusing assembly 290 aids to deliver or load the application material 270 through varying or changing the spray pattern of the application material 270. Hence, the application material 270 is selectively dispensed from the material application apparatus 210 to a predetermined portion of the implantable device along the dispensing path.

The dispensing path can include, for example, a sequential series of linear parallel passes that traverse back and forth along one axis of the implantable device 280. The relative motion can be continued in a linear manner between forward and backward or right to left and left to right or upward and downward, depending on the frame of reference. A traversal or a pass can be completed when the relative motion reverses direction. That is, relative motion continues past the implantable device 280, and then decelerates, stops, reverses direction and accelerates to a constant velocity. After each pass, the system 200 can adjust the position of the material delivery apparatus 210 and/or implantable device 280 relative to each other and can be changed or incremented to limit the possibility of application overlap, although a certain degree of overlap may be permitted.

Alternatively, the dispensing path created by the relative motion of the material delivery apparatus 210 and the implantable device 280 can include a single continuous helix that wraps continuously around the implantable device 280 tubular body and along the length of the implantable device 280. Alternatively, the dispensing path can include a non-continuous helix.

Figure 3:
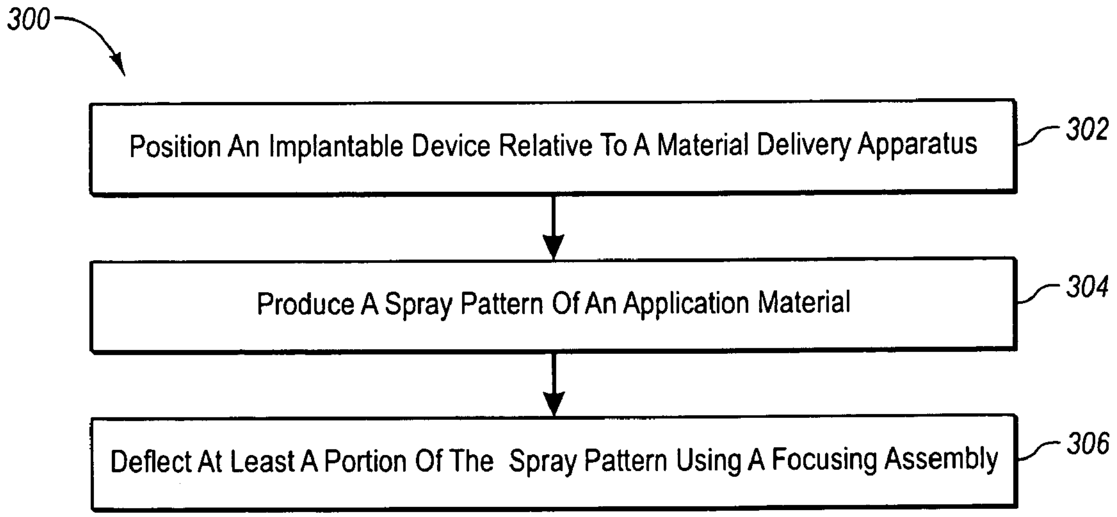
FIG. 3 illustrates an embodiment of a method for applying an application material to an implantable device, in accordance with the present invention.

FIG. 3 illustrates an embodiment of a method 300 for applying an application material to an implantable device, in accordance with the present invention. In the present embodiment, the method 300 may be used in conjunction with components of the system 100 described in connection with FIGS. 1 and 2 and/or any other system for applying an application material to an implantable device described herein. For example, the material delivery apparatus 110, focusing assembly 190, and/or the implantable device 180 may be used.

An implantable device may be positioned relative to a material delivery apparatus, as represented by block 302. Positioning an implantable device relative to a material delivery apparatus may include positioning the implantable device in a desired location and/or in a desired orientation. For example, a stent may be positioned about 30 mm from a nozzle of a material delivery apparatus and/or oriented perpendicular to the application material being applied.

In some embodiments, before and/or during the application of the application material to the implantable device, a focusing assembly may be positioned relative to the material delivery apparatus and/or the implantable device.

A spray pattern of an application material may be produced, as represented by block 304. The spray pattern of the application material may be produced by the material delivery apparatus. Producing a spray pattern may include applying the application material to the implantable device. Applying the application material to the implantable device may include moving the implantable device and/or the material delivery apparatus with respect to each other. For example, the material delivery apparatus may move along a length of the implantable device and the implantable device may rotate to facilitate a generally uniform application of the application material.

At least a portion of the spray pattern of the application material may be deflected, as represented by block 306. The focusing assembly may be used to deflect at least a portion of the spray pattern. Deflecting at least a portion of the spray pattern may include focusing the spray pattern to reduce the amount of application material that may be lost due to overspray and/or other factors.

Figure 4:
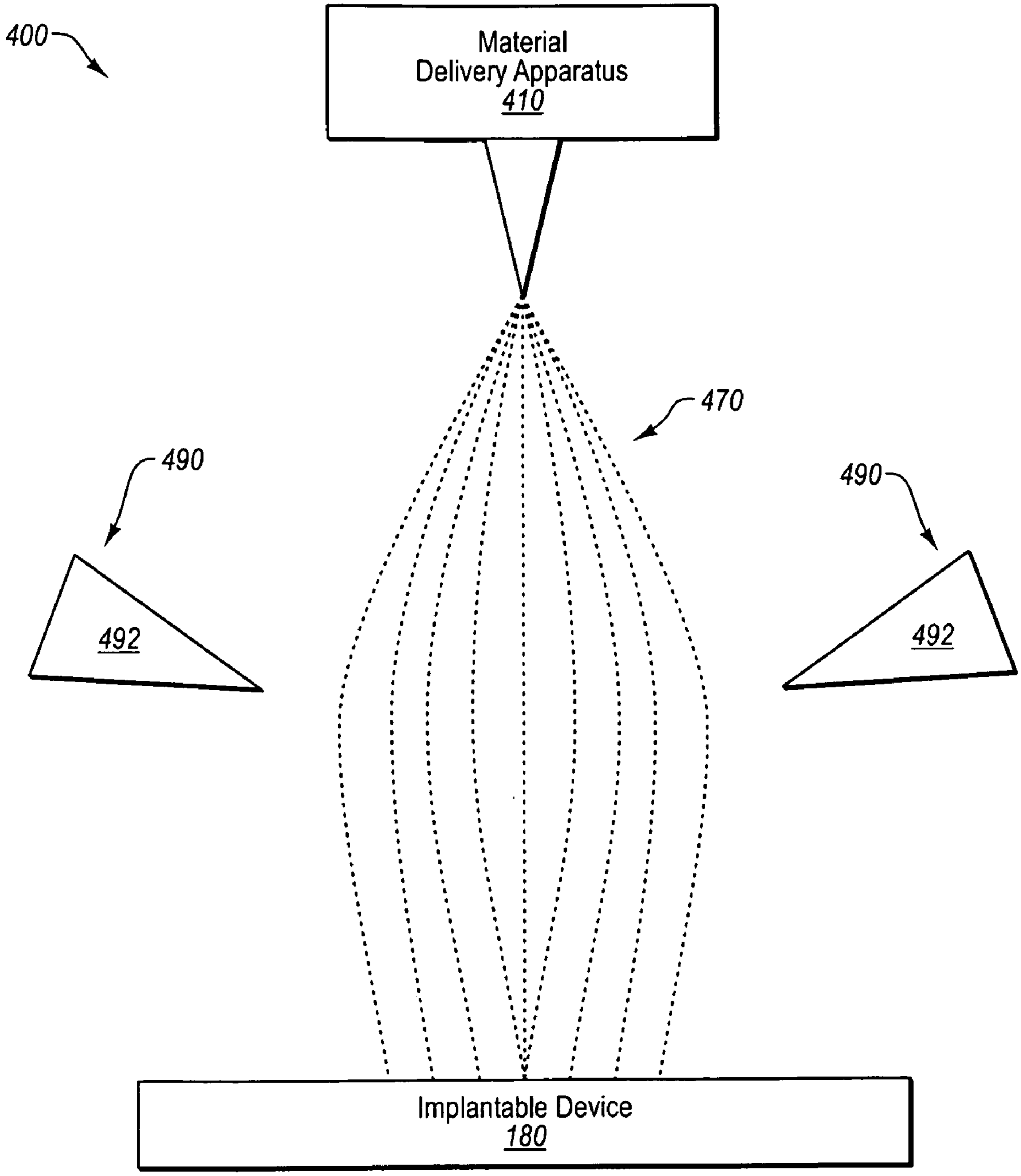
FIG. 4 illustrates a block diagram of another embodiment of a system for applying an application material to an implantable device, in accordance with the present invention.

FIG. 4 illustrates a block diagram of another embodiment of a system 400 for applying an application material 470 to an implantable device 180, in accordance with the present invention. The system 400 of this other embodiment may be functionally similar to that of the systems 100, 200 previously described above and shown in FIGS. 1 and 2 in most respects, wherein certain features will not be described in relation to this other embodiment wherein those components may function in the manner as described above and are hereby incorporated into this alternative embodiment described below.

The system 400 includes a material delivery apparatus 410 that may apply an application material 470 to an implantable device 180 and a focusing assembly 490 that may deflect a spray pattern of the application material 470. The focusing assembly 490, in the present embodiment, may include a plurality of focusing jets 492. The focusing jets 492 may deflect a spray pattern of the application material 470.

Figure 5:
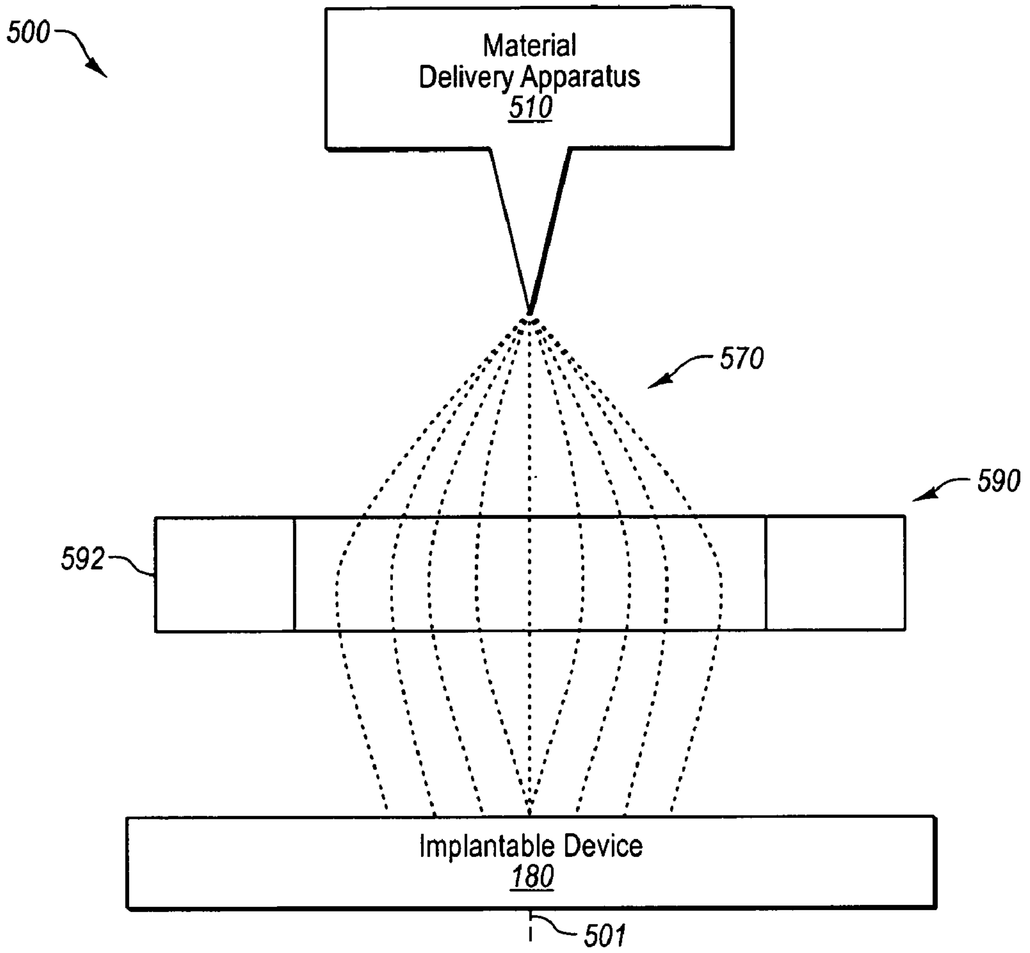
FIG. 5 illustrates a block diagram of a further embodiment of a system for applying an application material to an implantable device, in accordance with the present invention.

FIG. 5 illustrates a block diagram of a further embodiment of a system 500 for applying an application material 570 to an implantable device 180, in accordance with the present invention. The system 500 of this other embodiment may be functionally similar to that of the systems 100, 200, 400 previously described above and shown in FIGS. 1, 2, and 4 in most respects, wherein certain features will not be described in relation to this further embodiment wherein those components may function in the manner as described above and are hereby incorporated into this alternative embodiment described below.

The system 500 includes a material delivery apparatus 510 that may apply an application material 570 to an implantable device 180 and a focusing assembly 590 that may deflect a spray pattern of the application material 570.

The focusing assembly 590 may include an annular focusing jet 592. The annular focusing jet 592 may deflect the spray pattern of the application material 570. In the present embodiment, the annular focusing jet 592 may deflect the spray pattern of the application material 570 towards a central axis 501. Deflecting the spray pattern of the application material 570 towards a central axis 501 may focus the spray pattern to reduce the amount of application material 570 that may otherwise be wasted when applying the application material 570 without a focusing assembly 590.

Figure 6:
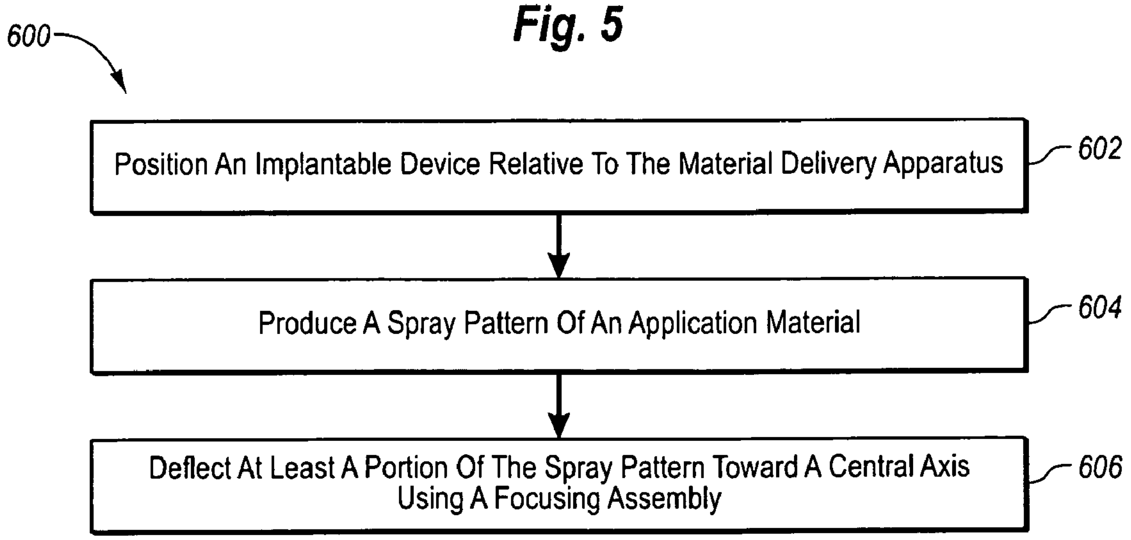
FIG. 6 illustrates an embodiment of another method for applying an application material to an implantable device, in accordance with the present invention.

FIG. 6 illustrates another embodiment of a method 600 for applying an application material to an implantable device, in accordance with the present invention. In the present embodiment, the method 600 may be used in conjunction with components of the systems 100, 200, 400, 500 described in connection with FIGS. 1, 2, 4, and 5 and/or any other system for applying an application material to an implantable device described herein. For example, a spray pattern in an application material may be deflected using a focusing assembly, including a single focusing jet 192, a plurality of focusing jets 492, an annular focusing jet 592, and/or combinations thereof.

The method 600 of this other embodiment may be functionally similar to the method 300 previously described above and shown in FIG. 3 in most respects, wherein certain features will not be described in relation to this other embodiment wherein those method components may be performed in the manner as described above and are hereby incorporated into this alternative embodiment described below.

An implantable device may be positioned relative to a material delivery apparatus, as represented by block 602. A spray pattern of an application material may be produced, as represented by block 604.

At least a portion of the spray pattern of the application material may be deflected toward a central axis, as represented by block 606. The focusing assembly may be used to deflect at least a portion of the spray pattern. Deflecting at least a portion of the spray pattern toward a central axis may include focusing the spray pattern to reduce the amount of application material that may be lost due to overspray and/or other factors.

Figure 7:
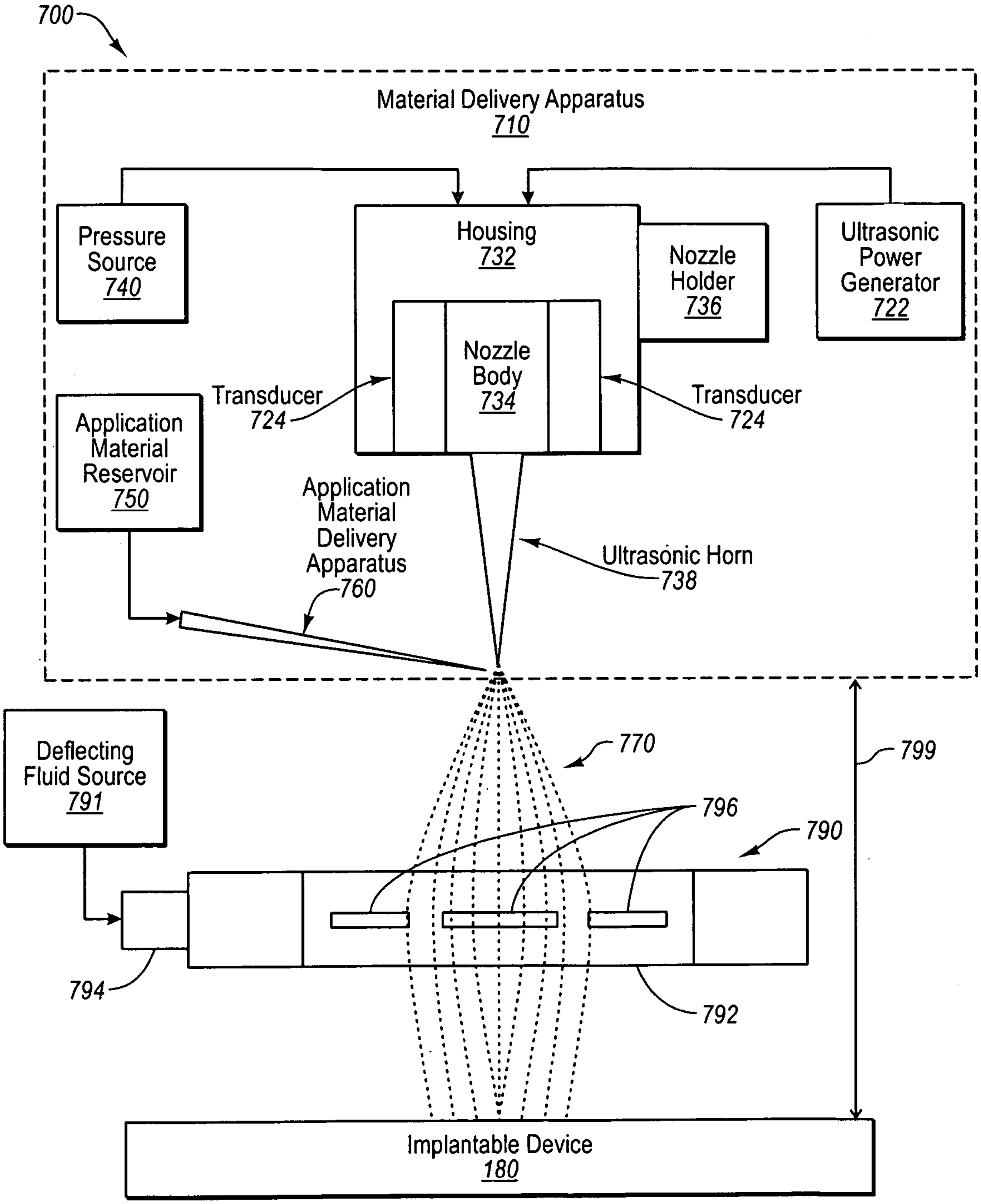
FIG. 7 illustrates a block diagram of a still further embodiment of a system for applying an application material to an implantable device, in accordance with the present invention.

FIG. 7 illustrates a block diagram of a still further embodiment of a system 700 for applying an application material 770 to an implantable device 180, in accordance with the present invention. The system 700 of this still further embodiment may be functionally similar to that of the systems 100, 200, 400, 500 previously described above and shown in FIGS. 1, 2, 4, and 5 in many respects, wherein certain features will not be described in relation to this still further embodiment wherein those components may function in the manner as described above and are hereby incorporated into this alternative embodiment described below.

The system 700 includes a material delivery apparatus 710 that may apply an application material 770 to an implantable device 180 and a focusing apparatus 790 that may deflect a spray pattern of the application material 770. The material delivery apparatus 710, in the present embodiment, may be an ultrasonic material delivery apparatus that may include an ultrasonic power generator 722, a transducer 724, a housing 732, a nozzle body 734, a nozzle holder 736, an ultrasonic horn 738, a pressure source 740, an application material reservoir 750, and/or an application material delivery apparatus 760. Ultrasonic horn 738 may be hollow and have a transport gas from pressure source 740 passing through to increase the velocity of the dispersed droplets.

The system 700, in the present embodiment, may include an ultrasonic generator. The ultrasonic generator may include an ultrasonic power generator 722 and at least one transducer 724. The ultrasonic power generator 722 may generate high frequency electrical energy. High frequency electrical energy may be generated in the range, for example, from about 25 kHz to about 120 kHz. The frequency may be determined based on the characteristics of the nozzle body 734 and/or ultrasonic horn 738.

The ultrasonic power generator 722 may be in electrical communication (not shown) with at least one transducer 724. The at least one transducer 724 (a cylindrical transducer 724 in the present embodiment) may convert the electrical energy generated by the ultrasonic power generator 722 into mechanical (i.e. vibration) energy. The transducers 724 may include piezoelectric transducers to facilitate in atomizing the application material 770.

The housing 732 may house the nozzle body 734. The housing 732 may be connected to the nozzle holder 736. The nozzle holder 736 may be used to position the material delivery apparatus 710 with respect to the implantable device 180 and/or focusing assembly 790.

In the present embodiment, the material delivery apparatus 710 may include both an application material delivery apparatus 760 and a nozzle body 734 and ultrasonic horn 738. In other embodiments, other configurations may be used. For example, the nozzle body 734 and ultrasonic horn 738 may be in fluid communication with the application material reservoir 750 and a pressure source 740.

The nozzle body 734 and/or the ultrasonic horn 738, in the present embodiment, may be in fluid communication with a pressure source 740. The pressure source 740, in the present embodiment, may include an air pressure source. The pressure source 740 may generate a pressurized fluid that may be shaped and/or directed by the nozzle body 734 and/or the ultrasonic horn 738. The pressure source 740, in the present embodiment, may generate a low-pressure air stream.

The application material delivery apparatus 760 may be connected to an application material reservoir 750. The application material reservoir 750 may include a pump, pressurized reservoir, gravity system, and/or other delivery mechanism to direct the application material 770 to the application material delivery apparatus 760. The application material delivery apparatus 760 may include a hypotube. The application material delivery apparatus 760 may deliver the application material 770 to the ultrasonic horn 738 to facilitate atomization of the application material 770.

The focusing assembly 790 may include an annular focusing jet 792. The annular focusing jet 792 may include an input port 794 and/or at least one opening 796, through which a deflecting fluid used to deflect the spray pattern of the application material 770 may be directed. The input port 794 may be in fluid communication with a deflecting fluid source 791.

The input port 794 and at least one opening 796 may be separated by a chamber (not shown). The chamber may facilitate a general evening and/or distribution of the pressure applied to the deflecting fluid, with a consequent evening of flow rate.

In the present embodiment, the at least one opening 796 may be located along the inner surface of the annular focusing jet 792. The at least one opening 796 may include a dimension that is smaller than a dimension of the chamber and/or a dimension of the input port 794. The at least one opening 796 of the annular focusing jet 792 may be circumferentially uniform. An opening 796 may include a pin-hole opening, a slot, a collection of pores, and/or other types of openings.

The annular focusing jet 792 may deflect the spray pattern of the application material 770. Similar to the previous embodiments, the annular focusing jet 792 may deflect the spray pattern of the application material 770 towards a central axis (not shown) and/or toward the implantable device 180. Deflecting the spray pattern of the application material 770 towards a central axis and/or toward the implantable device 180 may focus the spray pattern to reduce the amount of application material 770 that may be wasted when applying the application material 770 without a focusing assembly 790.

The material delivery apparatus 710 and the implantable device 180 may be separated by a predetermined distance 799. For example, a stent may be positioned about 30 mm from a nozzle of a material delivery apparatus.

Figure 8:
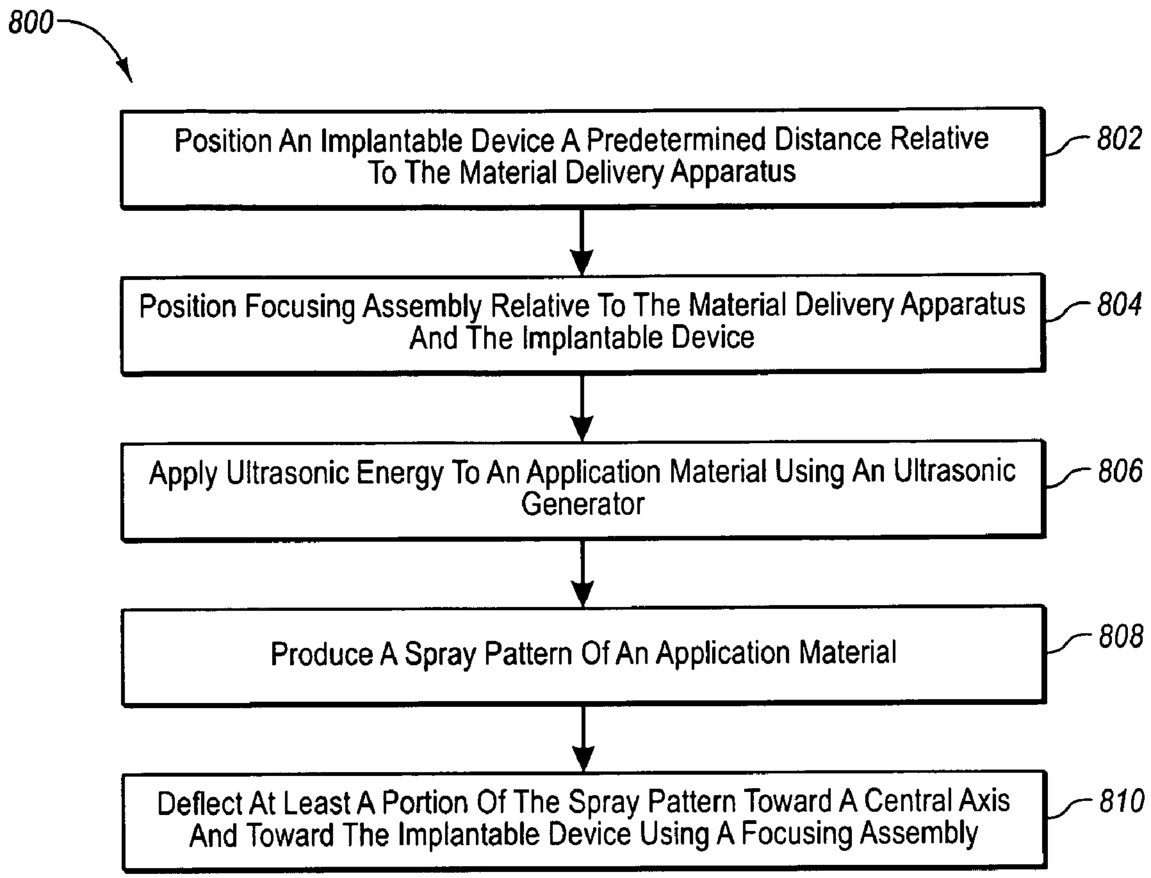
FIG. 8 illustrates a further embodiment of a method for applying an application material to an implantable device, in accordance with the present invention.

FIG. 8 illustrates a further embodiment of a method 800 for applying an application material to an implantable device, in accordance with the present invention. Systems for applying a coating to an implantable device may include the systems 100, 200, 400, 500, 700 previously described above and shown in FIGS. 1, 2, 4, 5, and 7 and/or any other system for applying an application material to an implantable device described herein. Components of these systems 100, 200, 400, 500, 700 may include a material delivery apparatus 110 (or components of a material delivery apparatus 710 such as an application material delivery apparatus 760, a transducer 724, an ultrasonic power generator 722, and/or other system components), an implantable device 180, a positioning assembly 212, and/or a focusing assembly 190 (or components of a focusing assembly 190, 790 such as a focusing jet 192 and/or an annular focusing jet 792).

The method 800 of this still further embodiment may be functionally similar to that of the methods 300, 600 previously described above and shown in FIGS. 3 and 6 in most respects, wherein certain features will not be described in relation to this still further embodiment wherein those method components may be performed in the manner as described above and are hereby incorporated into this further embodiment described below.

An implantable device may be positioned a predetermined distance relative to a material delivery apparatus, as represented by block 802. The predetermined distance may be determined to facilitate at least partial drying of at least a portion of the application material. Partial drying of at least a portion of the application material may reduce the amount of potential coating defects (i.e. webbing, cobwebs, and/or other defects).

Before and/or during the application of the application material to the implantable device, a focusing assembly may be positioned relative to the material delivery apparatus and/or the implantable device, as represented by block 804. The position of the focusing assembly may be determined based on a variety of factors including the desired spray pattern size as the application material contacts the implantable device.

Ultrasonic energy may be applied to an application material using an ultrasonic generator, as represented by block 806. The ultrasonic generator used may include the ultrasonic power generator 722 and/or at least one transducer 724 described above.

A spray pattern of an application material may be produced, as represented by block 808. For example, the spray pattern may be produced by the application material delivery apparatus 760 and/or the ultrasonic horn 738. At least a portion of the spray pattern of the application material may be deflected toward a central axis and toward the implantable device, as represented by block 810. Deflecting at least a portion of the spray pattern may include generally deflecting the spray pattern toward a central axis and/or toward the implantable device.

The invention is susceptible to various modifications and alternative means, and specific examples thereof have been shown by way of example in the drawings and are herein described in detail. It should be understood, however, that the invention is not to be limited to the particular devices or methods disclosed, but to the contrary, the invention is to cover all modifications, equivalents, and alternatives falling within the spirit and scope of the claims.

What is claimed is:

1. A method of coating an implantable device, the method comprising:

positioning an implantable device relative to a material delivery apparatus including a nozzle;

producing a spray pattern of an application material from the nozzle using the material delivery apparatus; and deflecting at least a portion of the spray pattern using a focusing assembly comprising an annular focusing jet, the annular focusing jet receives a deflecting fluid through an input port and directs the fluid from a chamber through at least one opening along an inner surface of the focusing jet.

2. The method of claim 1, wherein the annular focusing jet deflects at least a portion of the spray pattern toward a central axis.

3. The method of claim 1, wherein the annular focusing jet deflects at least a portion of the spray pattern toward the implantable device.

4. The method of claim 1, wherein positioning an implantable device relative to a material delivery apparatus further comprises positioning the implantable device a predetermined distance relative to the material delivery apparatus.

5. The method of claim 4, wherein the predetermined distance is selected to facilitate at least partial drying of the application material prior to contact with the implantable device.

6. The method of claim 1, wherein the implantable device is moved relative to a material delivery apparatus during spraying by a combination of translation and/or rotational motion.

7. The method of claim 1, further comprising positioning the annular focusing jet relative to the material delivery apparatus and the implantable device.

8. The method of claim 1, wherein the annular focusing jet deflects at least a portion of the spray pattern using at least one deflecting fluid selected from the group consisting of air, dry air, nitrogen, argon, helium, neon, carbon dioxide, oxygen, sulfur hexafluoride, water vapor, and gas at a controlled humidity.

9. The method of claim 8, wherein the deflecting fluid used to direct the application material is above ambient temperature to facilitate drying.

10. The method of claim 1, the material delivery apparatus further comprising an ultrasonic generator and a material delivery device, the ultrasonic generator being configured to atomize at least a portion of the application material.

11. The method of claim 1, wherein the application material includes a radiopaque material.

12. The method of claim 1, wherein the application material includes a contrast agent for magnetic resonance imaging.

13. The method of claim 1, wherein the application material includes a solvent.

14. The method of claim 1, wherein the application material includes a polymeric material.

15. The method of claim 1, wherein the application material is atomized by ultrasonic energy, by application of a high-pressure stream of gas, by centrifugal action, by electric potential, and/or by other atomization processes.

16. The method of claim 1, wherein the application material includes at least one bioactive agent that is an anti-proliferative, anti-inflammatory, antineoplastic, antiplatelet, anti-coagulant, anti-fibrin, antithrombonic, antimitotic, antibiotic, antiallergic or antioxidant drug.

17. The method of claim 1, wherein the implantable device is a closure element.

18. The method of claim 1, wherein the implantable device is a stent.

19. A method of coating an implantable device, the method comprising:

positioning an implantable device relative to a material delivery apparatus;

producing a spray pattern of an application material using the material delivery apparatus; and deflecting at least a portion of the spray pattern using a focusing assembly comprising an annular focusing jet, the annular focusing jet receives a deflecting fluid through an input port and directs the fluid from a chamber through at least one opening along an inner surface of the focusing jet.

20. The method of claim 19, wherein the at least one opening has a dimension that is smaller than a dimension of the chamber and/or a dimension of the input port.

21. The method of claim 19, wherein the at least one opening of the annular focusing jet is circumferentially uniform.

* * * * *